United States Patent
Vodyanyk et al.

(10) Patent No.: US 7,615,374 B2
(45) Date of Patent: Nov. 10, 2009

(54) GENERATION OF CLONAL MESENCHYMAL PROGENITORS AND MESENCHYMAL STEM CELL LINES UNDER SERUM-FREE CONDITIONS

(75) Inventors: Maksym A. Vodyanyk, Madison, WI (US); Junying Yu, Madison, WI (US); James A. Thomson, Madison, WI (US); Igor I. Slukvin, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/024,770

(22) Filed: Feb. 1, 2008

(65) Prior Publication Data
US 2009/0081784 A1 Mar. 26, 2009

Related U.S. Application Data

(60) Provisional application No. 60/974,980, filed on Sep. 25, 2007, provisional application No. 60/989,058, filed on Nov. 19, 2007.

(51) Int. Cl.
*C12N 5/00* (2006.01)
*C12N 15/00* (2006.01)

(52) U.S. Cl. ...................... 435/455; 435/325
(58) Field of Classification Search .................. 435/455, 435/325
See application file for complete search history.

(56) References Cited

U.S. PATENT DOCUMENTS
2006/0008902 A1  1/2006  Pike et al.

OTHER PUBLICATIONS
Sotiropoulou, Stem Cells, 2006, vol. 24, p. 1409-1410.*
Meuleman, Eur. J. Haematol., 2006, vol. 76, p. 309-316.*
Olivier, Stem Cells, 2006, vol. 24, p. 1914-1922.*
Barberi T, et al. "Derivation of multipotent mesenchymal precursors from human embryonic stem cells," PLoS Med. 2: e161 (2005).
Korhonen M, "Culture of human mesenchymal stem cells in serum-free conditions: no breakthroughs yet," Eur. J. Haematol. 77:167 (2007).
Meuleman N, et al., "Human marrow mesenchymal stem cell culture: serum-free medium allows better expansion than classical alpha-minimal essential medium (MEM)," Eur. J. Haematol. 76:309-316 (2006).
Meuleman N, et al., "Human marrow mesenchymal stem cell culture: serum-free medium allows better expansion than classical alpha-minimal essential medium (MEM)," Eur. J. Haematol. 77:168 (2007).
Olivier E, et al., "Differentiation of human embryonic stem cells into mesenchymal stem cells," Blood (47th Annual Meeting of the American Society of Hematology) 106:Abstract 1389 (2005).
Olivier E, et al., "Differentiation of human embryonic stem cells into bipotent mesenchymal stem cells," Stem Cells 24:1914-1922 (2006).
Sotiropoulou P, et al., "Cell culture medium composition and translational adult bone marrow-derived stem cell research," Stem Cells 24:1409-1410 (2006).
Trivedi P & Hematti P, "Simultaneous generation of CD34+ primitive hematopoietic cells and CD56+ mesenchymal stem cells from human embryonic stem cells cocultured with murine OP9 stromal cells," Exp. Hematol. 35:146-154 (2007).
Trivedi P & Hematti P, "Derivation and immunological characterization of mesenchymal stromal cells from human embryonic stem cells," Exp. Hematol. 36:350-359 (2008).
Vodyanik M, et al., "Human embryonic stem cell-derived CD34+ cells: efficient production in the coculture with OP9 stromal cells and analysis of lymphohematopoietic potential," Blood 105:617-626 (2005).
Yu J, et al., "Induced pluripotent stem cell lines derived from human somatic cells," Science 318:1917-1920 (2007).

* cited by examiner

*Primary Examiner*—Michael C. Wilson
(74) *Attorney, Agent, or Firm*—Quarles & Brady LLP

(57) ABSTRACT

Methods for obtaining multipotent mesenchymal stem cells under serum-free conditions and methods for identifying multipotent mesenchymal progenitor cells are disclosed.

22 Claims, No Drawings

GENERATION OF CLONAL MESENCHYMAL PROGENITORS AND MESENCHYMAL STEM CELL LINES UNDER SERUM-FREE CONDITIONS

CROSS-REFERENCE TO RELATED APPLICATIONS

This application claims the benefit of U.S. Provisional Patent Application No. 60/974,980, filed Sep. 25, 2007; and U.S. Provisional Patent Application No. 60/989,058, filed Nov. 19, 2007, each of which is incorporated herein by reference as if set forth in its entirety.

STATEMENT REGARDING FEDERALLY SPONSORED RESEARCH OR DEVELOPMENT

This invention was made with United States government support awarded by the following agency: NIH RR052085 and NIH HD044067. The United States government has certain rights in this invention.

BACKGROUND

The invention relates generally to clonal primate mesenchymal progenitors and to mesenchymal stem cell (MSC) lines and methods for identifying and generating such cells, and more particularly to methods for generating clonal mesenchymal progenitors and MSC lines under serum-free conditions.

MSCs can differentiate into at least three downstream mesenchymal cell lineages (i.e., osteoblasts, chondroblasts and adipocytes). To date, no unique MSC marker has been identified. As such, morphological and functional criteria are used to identify these cells. See, Horwitz E, et al., "Clarification of the nomenclature for MSC: the International Society for Cellular Therapy position statement," Cytotherapy 7:393 (2005); and Dominici M, et al., "Minimal criteria for defining multipotent mesenchymal stromal cells. The International Society for Cellular Therapy position statement," Cytotherapy 8:315 (2006). Because MSCs can differentiate into many cell types, the art contemplates methods for differentiating MSCs for cell-based therapies, for regenerative medicine and for reconstructive medicine.

Typically, MSCs are isolated from adult bone marrow, fat, cartilage and muscle. Pittenger F, et al., "Multilineage potential of adult human mesenchymal stem cells," Science 284:143-147 (1999); Zuk P, et al., "Multilineage cells from human adipose tissue: implications for cell-based therapies," Tissue Eng. 7:211-228 (2001); and Young H, et al., "Human reserve pluripotent mesenchymal stem cells are present in the connective tissues of skeletal muscle and dermis derived from fetal, adult, and geriatric donors," Anat. Rec. 264:51-62 (2001). MSCs have also been isolated from human peripheral blood. Kassis I, et al., "Isolation of mesenchymal stem cells from G-CSF-mobilized human peripheral blood using fibrin microbeads," Bone Marrow Transplant. 37:967-976 (2006). MSCs can also be isolated from human neonatal tissue, such as Wharton's jelly (Wang H, et al., "Mesenchymal stem cells in the Wharton's jelly of the human umbilical cord," Stem Cells 22:1330-1337 (2004)), human placenta (Fukuchi Y, et al., "Human placenta-derived cells have mesenchymal stem/progenitor cell potential," Stem Cells 22:649-658 (2004)); and umbilical cord blood (Erices A, et al., "Mesenchymal progenitor cells in human umbilical cord blood," Br. J. Haematol. 109:235-242 (2000)) and human fetal tissues (Campagnoli C, et al., "Identification of mesenchymal stem/progenitor cells in human first-trimester fetal blood, liver, and bone marrow," Blood 98:2396-2402 (2001)).

The art is limited by an inability to isolate sufficient MSCs for subsequent differentiation and use. Where suitable donors are available, the invasive procedures required to isolate even a limited number of cells present risks to donors. It also remains difficult to maintain isolated MSCs in long-term culture and to maintain such cultures free of bacterial or viral contamination.

Efforts to devise methods for differentiating embryonic stem cells (ESCs) including human ESCs (hESCs) to MSCs either have required culturing the cells in a medium containing potentially contaminating serum or have yielded cells that retain characteristics of undifferentiated hESCs. For example, Barberi et al. differentiated hESCs to MSCs on mitotically-inactivated mouse stromal cell lines (i.e., feeder cells) with 20% heat-inactivated fetal bovine serum (FBS) in alpha MEM medium for 40 days. Barberi T, et al. "Derivation of multipotent mesenchymal precursors from human embryonic stem cells," PLoS Med. 2:e161 (2005). Cells were harvested and assayed for CD73, and $CD73^+$ cells were then plated in the absence of the feeder cells with 20% FBS in alpha MEM for 7 to 10 days. Barberi et al. differentiated the MSCs into adipogenic cells, chondrogenic cells, osteogenic cells and myogenic cells.

Likewise, Olivier et al. differentiated hESCs to MSCs by plating raclures (i.e., spontaneously differentiated cells that appear in hESC culture in the center or at the edges of colonies) with D10 medium (DMEM, 10% FBS, 1% penicillin/streptomycin and 1% non-essential amino acids) changed weekly until a thick, multi-layer epithelium developed. Olivier E, et al., "Differentiation of human embryonic stem cells into bipotent mesenchymal stem cells," Stem Cells 24 1914-1922 (2006). After approximately four weeks, MSCs were isolated by dissociating the epithelium with a mixture of trypsin, collagenase type IV and dispase for four to six hours, followed by re-plating in D10 medium. Olivier et al.'s MSCs grew robustly, had stable karyotypes, were contact inhibited, senesced after twenty passages and differentiated into adipogenic and osteogenic cells. Olivier et al. did not report that the cells differentiated into chondroblasts. Unlike Barberi et al., Olivier et al. did not require feeder cells to support differentiation of hESC to MSCs. However, Olivier et al.'s MSCs were SSEA-4 positive, suggesting that these MSCs expressed cell surface markers characteristic of hESC.

Pike & Shevde differentiated hESCs to MSCs via embryoid bodies (EBs) incubated for ten to twelve days in a mesenchymal-specific medium (MesenCult® medium with 10% FBS; alpha MEM with glutamine and nucleosides; or DMEM with glucose and glutamine, replaced every two days). US Patent Publication No. 2006/0008902. The EBs were digested, and pre-mesenchymal cells were cultured to 80% confluence. The cells were trypsinized and passaged three times in mesenchymal-specific medium.

Meuleman et al. reported culturing MSCs in a serum-free medium; however, it was later discovered that the medium did in fact contain animal serum as a component. Meuleman N, et al., "Human marrow mesenchymal stem cell culture: serum-free medium allows better expansion than classical alpha-minimal essential medium (MEM)," Eur. J. Haematol. 76:309-316 (2006); and Meuleman N, et al., "Human marrow mesenchymal stem cell culture: serum-free medium allows better expansion than classical alpha-minimal essential medium (MEM)," Eur. J. Haematol. 77:168 (2007); but see, Korhonen M, "Culture of human mesenchymal stem cells in serum-free conditions: no breakthroughs yet," Eur. J. Haematol. 77:167 (2007).

Those methods cultured and differentiated MSCs in serum-containing medium. Serum-free conditions for culturing and differentiating MSCs, if defined, would reduce variation among batches and eliminate a risk of infection transmitted by xenogenic by-products and pathogens. Sotiropoulou P, et al., "Cell culture medium composition and translational adult bone marrow-derived stem cell research," Stem Cells 24:1409-1410 (2006).

For the foregoing reasons, there is a need for new methods for obtaining early mesenchymal progenitors and MSCs, especially when derived under serum-free conditions.

BRIEF SUMMARY

In a first aspect, the invention is summarized in that a method of generating a clonal population of primate MSCs includes the steps of culturing a heterogeneous, single-cell suspension of primate cells that contains mesenchymal progenitors in a serum-free, semi-solid medium containing between about 5 and about 100 ng/ml bFGF until independent colonies form, and culturing one of the independent colonies in a serum-free, liquid medium containing between about 5 and about 100 ng/ml, or at about 5 ng/ml, or between about 20 and about 100 ng/ml, bFGF to obtain an substantially pure clonal population of MSCs.

The heterogeneous suspension for use in the method can be obtained, for example, by differentiating pluripotent cells from a primate (e.g., human), such as ESCs or induced pluripotent stem (iPS) cells, in culture until cells in the culture are mesenchymal progenitors. This can be accomplished by co-culturing the pluripotent cells with bone marrow stromal cells in a medium that supports differentiation as described herein for at least two to five days, or by dissociating EBs, which can themselves be obtained by culture of pluripotent cells using well-known methods, to single cells, and then suspending the cells as a single cell suspension. The bone marrow stromal cells can be mouse OP9 cells. A heterogeneous suspension substantially free of some or all cells not derived by in vitro differentiation of pluripotent cells (especially co-cultured bone marrow cells) can be obtained by depleting those cells from the suspension. These cells can be depleted from the suspension before use, for example, by non-covalently binding the cells to be depleted to paramagnetic monoclonal antibodies specific for the epitopes on the cells to be depleted and then segregating the antibody-bound cells with a magnet. Cells in a suspension obtained from pluripotent cells can express at least MIXL1 and T (BRACHYURY).

The medium can be rendered semi-solid by including about 1% methylcellulose in the medium. The medium can optionally contain between about 10 and about 20 ng/ml PDGF-BB. The suspension can be cultured for between about ten to about twenty days or more to produce the colonies.

Mesenchymal progenitors are identified as having been present in the suspension if mesenchymal colonies form during culture in the serum-free, semi-solid medium supplemented with bFGF. The colonies obtained in the method can be identified as mesenchymal by their expression of at least a plurality of FOXF1, MEF2C, MSX1, MSX2, SNAI1, SNAI2, SOX9 and RUNX2. Characteristics of the colonies include functional, morphological and phenotypical characteristics and gene expression profile. Functional characteristics of the colonies include (1) growth stimulation by factors that promote mesenchymal cell growth (e.g., PDGF-BB, EGF and TGF-alpha) and growth suppression by factors involved in mesodermal differentiation (e.g., VEGF, TGF-beta and Activin A); and (2) differentiation into osteogenic, chondrogenic or adipogenic cell lineages. Morphological characteristics of the colonies include (1) tight packing of cells to form round aggregates measuring 100-500 µm in diameter and (2) even after prolonged culture, lack of dense outer cell layer and irregular inner structure, which are characteristics of EBs. Phenotypical characteristics of the colonies include (1) expression of CD44, CD56, CD105 and CD140a (PDGFRA), but not hematoendothelial surface markers (i.e., CD31, CD43, CD45 and VE-cadherin); (2) expression of FOXF1, MEF2C, MSX1, MSX2, SNAI1, SNAI2, SOX9 and RUNX2; and (3) expression of vimentin and alpha smooth muscle actin.

The mesenchymal colonies thus formed in the method can be further cultured in the presence of an extracellular matrix protein, such as Matrigel®, collagen, gelatin or fibronectin, as well as combinations thereof.

The invention is further summarized as an substantially pure population of clonally-derived MSC lines produced from the methods described above that are positive for at least CD44, CD56, CD105 and CD140a, but negative for CD31, CD43, CD45 and VE-cadherin.

The described embodiments have many advantages, including that mesenchymal progenitors or MSCs obtained in the methods may be used to treat diseases associated with bone, cartilage and fat cells.

It is also an advantage that a clonal population of MSCs can be obtained from a single mesenchymal colony.

It is also an advantage that the cells obtained in the methods can easily be selected for further expansion because the mesenchymal progenitors have high proliferation potential and form large colonies.

It is yet another advantage that cells obtained in the methods can be non-immunoresponsive to allo- and auto-antigens on transplantation.

It is still another advantage that the cells obtained in the methods can differentiate into at least osteogenic, chondrogenic and adipogenic lineages.

These and other features, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

BRIEF DESCRIPTION OF THE DRAWINGS

Not applicable.

DESCRIPTION OF EXEMPLARY EMBODIMENTS

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

In describing the embodiments and claiming the invention, the following terminology is used in accordance with the definitions set out below.

As used herein, "about" means within 5% of a stated concentration.

As used herein, "clonal" means a population of cells cultured from a single cell, not from an aggregate of cells. Cells in a "clonal population" display a substantially uniform pattern of cell surface markers and morphology and are substantially genetically identical.

As used herein, an "embryoid body" or an "EB," is an aggregate of cells derived from pluripotent cells, such as ESCs or iPS cells, where cell aggregation can be initiated by hanging drop, by plating upon non-tissue culture treated plates or spinner flasks (i.e., low attachment conditions); any method prevents the cells from adhering to a surface to form typical colony growth. EBs appear as founded collections of cells and contain cell types derived from all three germ layers (i.e., the ectoderm, mesoderm and endoderm). Methods for generating EBs are well-known to one ordinary skill in the art. See, Itskovitz-Eldor J, et al., "Differentiation of human embryonic stem cells into embryoid bodies compromising the three embryonic germ layers," Mol. Med. 6:88-95 (2000); Odorico J, et al., Stem Cells 19:193-204 (2001); and U.S. Pat. No. 6,602,711, each of which is incorporated herein by reference as if set forth in its entirety.

As used herein, "serum-free" means that neither the culture nor the culture medium contains serum or plasma, although purified or synthetic serum or plasma components (e.g., FGFs) can be provided in the culture in reproducible amounts as described below.

As used here, a "substantially pure population" means a population of derived mesenchymal cells that contains at least 99% mesenchymal cells. Cell purification can be accomplished by any means known to one of ordinary skill in the art. For example, a substantially pure population of cells can be achieved by growth of cells or by selection from a less pure population, as described herein.

As used herein, "pluripotent cells" means a population of cells capable of differentiating into all three germ layers and becoming any cell type in the body. Pluripotent cells express a variety of cell surface markers, have a cell morphology characteristic of undifferentiated cells and form teratomas when introduced into an immunocompromised animal, such as a SCID mouse. Teratomas typically contain cells or tissues characteristic of all three germ layers.

As used herein, "multipotent" cells are more differentiated than pluripotent cells, but are not permanently committed to a specific cell type. Pluripotent cells therefore have a higher potency than multipotent cells.

As used herein, "induced pluripotent stem cells" or "iPS cells" are cells that are differentiated, somatic cells reprogrammed to pluripotency. The cells are substantially genetically identical to their respective differentiated somatic cell of origin and display characteristics similar to higher potency cells, such as ES cells. See, Yu J, et al., "Induced pluripotent stem cell lines derived from human somatic cells," Science 318:1917-1920 (2007), incorporated herein by reference as if set forth in its entirety.

As used herein, a "mesenchymal stem cell," "MSC," or "mesenchymal progenitor" is a cell capable of differentiating into the mesenchymal cell lineages (i.e., osteoblasts, chondroblasts and adipocytes). As noted above, no unique MSC marker has been identified. As such, morphological and functional criteria well-known to those of ordinary skill in the art are used to identify these cells. See, Horwitz et al., supra; Dominici et al., supra; Trivedi P & Hematti P, "Derivation and immunological characterization of mesenchymal stromal cells from human embryonic stem cells," Exp. Hematol. Jan. 5, 2008 [Epub ahead of print]; Trivedi P & Hematti P, "Simultaneous generation of CD34+ primitive hematopoietic cells and CD56+ mesenchymal stem cells from human embryonic stem cells cocultured with murine OP9 stromal cells," Exp. Hematol. 35:146-154 (2007); and US Published Patent Application No. 2006/0008902, each of which is incorporated herein by reference as if set forth in its entirety. MSCs produced by the methods described herein can be characterized according to phenotypic criteria. For example, mesenchymal progenitors or MSCs can be recognized by their characteristic mononuclear ovoid, stellate shape or spindle shape, with a round to oval nucleus. The oval elongate nuclei typically have prominent nucleoli and a mix of hetero- and euchromatin. These cells have little cytoplasm, but many thin processes that appear to extend from the nucleus. It is believed that mesenchymal progenitors or MSCs will typically stain for one, two, three or more of the following markers: CD106 (VCAM), CD166 (ALCAM), CD29, CD44 and alkaline phosphatase, while being negative for hematopoietic lineage cell markers (e.g., CD14 or CD45) and endothelial lineage cell markers. (e.g., CD31 and VE-cadherin). Mesenchymal progenitors or MSCs may also express STRO-1 as a marker.

It is contemplated that Matrigel®, laminin, collagen (especially collagen type I), fibronectin and glycosaminoglycans may all be suitable as an extracellular matrix, by themselves or in various combinations.

The invention will be more fully understood upon consideration of the following non-limiting Examples.

EXAMPLES

Example 1

Generation of MSCs from hESCs Under Serum-Free Conditions hESCs (H1; WiCell; Madison, Wis.) were maintained on irradiated mouse embryonic fibroblasts in a serum-free medium, such as DMEM/F12 medium supplemented with 20% Knockout™ serum replacer, 2 mM L-glutamine, 1× (100 μM) non-essential amino acids, 100 μM 2-mercaptoethanol and 4 ng/ml bFGF (all from Gibco-Invitrogen; Carlsbad, Calif.). See Amit M, et al., "Clonally derived human embryonic stem cell lines maintain pluripotency and proliferative potential for prolonged periods of culture," Dev. Biol. 227:271-278 (2000), incorporated herein by reference as if set forth in its entirety. Mouse OP9 bone marrow stromal cells (kindly provided by Dr. Toru Nakano and available from ATCC, catalog # CRL-2749) were maintained by four-day subculture on gelatin-coated dishes in alpha MEM medium (Gibco-Invitrogen) with 20% fetal calf serum (FCS; HyClone; Logan, Utah).

The hESCs were induced to differentiate by co-culture with mouse OP9 bone marrow stromal cells, as previously described. Vodyanik M, et al., "Human embryonic stem cell-derived CD34+ cells: efficient production in the coculture with OP9 stromal cells and analysis of lymphohematopoietic potential," Blood 105:617-626 (2005), incorporated herein by reference as if set forth in its entirety. Briefly, small aggregates of hESCs were added to OP9 cells in alpha MEM supplemented with 10% FCS and 100 μM MTG (Sigma; St. Louis, Mo.). On the next day (day 1) of culture, the medium was changed, and the cultures were harvested on the days indicated below.

On day 2 of co-culture, mesodermal commitment was detected by a peak expression of transcription factors for mesendoderm (GSC, MIXL1 and T (BRACHYURY)) and early mesoderm (EVX1, LHX1 and TBX6) with Nimble-Gen® (Madison, Wis.) microarrays. Mesenchymal progenitors were still present in co-culture during days 3-5; however, some specification to endoderm and mesodermal lineages was also observed. This stage was accompanied with sustained expression of genes involved in epithelial-mesenchymal transition (EMT; SNAI1 and SNAI2) and cell expansion (HOXB2-3). It also coincided with a maximal cell proliferation rate in hESC/OP9 co-culture. Differentiation of specific mesendodermal lineages was observed on days 5-7 of co-culture, when markers of developing endoderm (AFP and SERPINA1), mesenchymal (SOX9, RUNX2 and PPARG2) and hematoendothelial (CDH5 and GATA1) cells were detected. However, muscle-inductive factors (MYOD1, MYF5 and MYF6) were not expressed throughout seven days of co-culture. Moreover, neuroectoderm (SOX1 and NEFL) or trophectoderm (CGB and PLAC) markers were not detected, indicating that OP9 cells provided an efficient inductive environment for directed hESC differentiation toward the mesendodermal pathway.

Also on day 2 of co-culture, a single-cell suspension was harvested from the co-culture by successive enzymatic treatment with collagenase IV (Gibco-Invitrogen) at 1 mg/ml in DMEM/F12 medium for 15 minutes at 37° C. and 0.05% Trypsin-0.5 mM EDTA (Gibco-Invitrogen) for 10 minutes at 37° C. Cells were washed 3 times with PBS-5% FBS, filtered through 70 μM and 30 μM cell strainers (BD Labware; Bedford, Mass.) and labeled with anti-mouse CD29-PE (AbD Serotec; Raleigh, N.C.) and anti-PE paramagnetic monoclonal antibodies (Miltenyi Biotec; Auburn, Calif.). The cell suspension was purified with magnet-activated cell sorting (MACS) by passing it through a LD magnetic column attached to a Midi-MACS separation unit (Miltenyi Biotech) to obtain a negative fraction of OP9-depleted, hESC-derived cells. Purity was verified using pan anti-human TRA-1-85 monoclonal antibodies (R&D Systems; Minneapolis, Minn.).

The purified single-cell suspension was plated at density of $2\times10^4$ cells/ml on a semisolid, serum-free medium composed of StemLine™ serum-free medium (Sigma; St. Louis, Mo.) supplemented with 5-100 ng/ml bFGF (PeproTech; Rocky Hill, N.J.) and 1% methylcellulose (Stem Cell Technologies; Vancouver, Canada) with or without 10-20 ng/ml PDGF-BB (PeproTech). PDGF-BB improved growth of mesenchymal cells, but was not essential for colony formation. After days 14-21 of culture, large, compact mesenchymal colonies formed that resembled embryoid bodies (EBs). Mesenchymal colonies were detected on day 7; however, 10-20 days were required to reveal actively growing colonies. No mesenchymal colonies were observed upon culture of undifferentiated hESCs or cells harvested on day 1 or on day 6 of co-culture.

Mesenchymal colonies, which appeared as embryoid-like bodies, were distinguished from EBs through several characteristics: (1) formation and growth under serum-free conditions supplemented with bFGF and stimulation by factors promoting mesenchymal cell growth (e.g., PDGF-BB, EGF and TGF-α), but suppression by factors involved in mesodermal differentiation (e.g., VEGF, TGF-β and Activin A) in mesenchymal colonies; (2) lack of a dense outer cell layer and irregular cavitated structure characteristic of EBs, even after prolonged culture in mesenchymal colonies; and (3) presence of morphological homogeneity in cells comprising the mesenchymal colonies.

To demonstrate that the single-cell suspensions did not form aggregates upon plating in semi-solid medium, clonality of the mesenchymal colonies obtained in the culture methods was tested and confirmed using chimeric hESC lines established from cells retrovirally marked with a reporter gene, e.g., either enhanced green fluorescent protein (EGFP) or histone 2B-(H2BB) mOrange fluorescent protein. Expression of a product of the reporter gene indicated clonality. The chimeric hESC lines were generated from two lentiviral constructs: (1) the EGFP protein expressed constitutively from an elongation factor 1 alpha (EF1alpha) promoter, and (2) the H2BB-mOrange protein expressed constitutively from the EF1alpha promoter. Both constructs were packaged in 293FT cells, and the lentiviruses were used to transduce H1 hESCs to produce stable H1 hESC lines that expressed either green EGFP protein or orange H2BB-mOrange protein. Mesenchymal colonies derived from the described methods were of single colors, either green or orange, thus indicating the clonal (i.e., single cell) origin of the MSCs.

In addition, prospective phenotypic analysis demonstrated a positive correlation between mesenchymal-colony forming cell (CFC) frequency and KDR (VEGFR2) expression, though $KDR^{high}CD34+$ population of the earliest hemangiogenic precursors was devoid of mesenchymal-CFCs. Analysis of cells within mesenchymal colonies revealed a homogeneous population of early mesenchymal cells defined by high CD90, CD140a and CD166 expression, low CD44, CD56 and CD105 expression and lack of CD24, CD31, CD43, CD45, CD144, and SSEA4 expression. In addition, mesenchymal colonies expressed vimentin and alpha smooth muscle actin. Furthermore, mesenchymal colonies expressed genes specific for MSC lineage, such as FOXF1, MSX1/2, SNAI1/2, SOX9, RUNX2 and MEF2C.

Individual mesenchymal colonies were transferred to wells of a collagen- or fibronectin-coated, 96-well plate pre-filled with 0.2 ml/well StemLine™ serum-free medium supplemented with 5-100 ng/ml bFGF. After 3-4 days of culture, adherent cells from individual wells were harvested by trypsin treatment and expanded on collagen- or fibronectin-coated dishes in StemLine™ serum-free medium with 5-100 ng/ml bFGF.

MSCs were expanded for many passages. When individual colonies were plated on collagen- or fibronectin-coated plates, immediate attachment and vigorous outgrowth of fibroblast-like cells were observed. During subsequent passages, cells grew intensively during the first 10 passages; however, growth rate was attenuated at passages 10-15 and gradual senescence was observed during passages 15-20.

Cell lines established from individual colonies were maintained in serum-free medium with bFGF for 10-15 passages at a high proliferation rate. Phenotypically, all cell lines displayed a mesenchymal phenotype as defined by expression of CD44, CD56, CD105 and CD140a (PDGFRA), but no expression of hematoendothelial markers (i.e. CD31, CD43, CD45 and VE-cadherin). When tested in conditions revealing mesenchymal differentiation potential, the cell lines were capable of osteogenic, chondrogenic and adipogenic differentiation. Interestingly, these cells resemble bone marrow MSCs, but expand and proliferate better than bone marrow MSCs.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of generating a clonal population of primate mesenchymal stem cells (MSCs), the method comprising the steps of:

culturing a heterogeneous, single-cell suspension of primate cells that contains mesenchymal progenitors in a serum-free, semi-solid medium containing between about 5 and about 100 ng/ml bFGF until independent colonies form; and culturing one of the independent colonies in a serum-free, liquid medium containing between about 5 and about 100 ng/ml bFGF to obtain an substantially pure clonal population of MSCs.

2. The method of claim 1, wherein the heterogeneous suspension is obtained in a method comprising the steps of:

co-culturing pluripotent primate cells with bone marrow stromal cells in a medium that supports differentiation for between two and five days until differentiated cells are formed; and suspending the differentiated cells.

3. The method of claim 2, wherein the pluripotent cells are selected from the group consisting of embryonic stem cells (ESCs) and induced pluripotent stem (iPS) cells.

4. The method of claim 2, wherein the bone marrow stromal cells are mouse OP9 cells.

5. The method of claim 1, wherein the heterogeneous suspension is obtained in a method comprising the steps of:

dissociating an embryoid body to single cells; and suspending the single cells.

6. The method of claim 1, wherein the single-cell suspension is cultured for between ten to twenty days.

7. The method of claim 1, wherein the semi-solid medium contains between about 20 and about 100 ng/ml bFGF.

8. The method of claim 1, wherein the semi-solid medium contains about 5 ng/ml bFGF.

9. The method of claim 1, wherein the semi-solid medium contains about 1% methylcellulose.

10. The method of claim 1, wherein the semi-solid medium contains between about 10 ng/ml and about 20 ng/ml PDGF-BB.

11. The method of claim 1, wherein cells in the single-cell suspension express MIXL1 and T.

12. The method of claim 1, wherein the primate cells are of human origin.

13. The method of claim 1, wherein the MSCs are cultured in the presence of an extracellular matrix protein.

14. The method of claim 13, wherein the extracellular matrix protein is selected from the group consisting of Matrigel®, collagen, gelatin and fibronectin.

15. The method of claim 1, wherein the independent colonies express FOXEF1, MEF2C, MSX1, MSX2, SNAI1, SNAI2, SOX9 and RUNX2.

16. The method of claim 1, wherein the mesenchymal colonies express CD44, CD56 and CD105 expression, but do not express CD31, CD43, CD45 and VE-cadherin.

17. The method of claim 1, wherein the method comprises the step of:

observing at least one mesenchymal characteristic of the independent colonies formed during culture in the serum-free, semi-solid medium, thereby confirming identification of mesenchymal progenitors in the suspension.

18. The method of claim 17 wherein the at least one mesenchymal characteristic is selected from the group consisting of a functional characteristic, a morphological characteristic and a phenotypical characteristic.

19. The method of claim 18, wherein the functional characteristic is selected from the group consisting of (1) growth stimulation by factors that promote mesenchymal cell growth and growth suppression by factors involved in mesodermal differentiation and (2) differentiation into osteogenic, chondrogenic or adipogenic cell lineages.

20. The method of claim 17, wherein the method further comprises counting colonies to estimate a number of mesenchymal progenitors in the heterogeneous suspension.

21. A cell population comprising:

an substantially pure line of clonally-derived mesenchymal stem cells positive at least for CD44, CD56, CD140a and CD105, but negative for CD31, CD43, CD45 and VE cadherin.

22. The cell population of claim 21, wherein the population comprises at least 99% mesenchymal stem cells.

* * * * *